(12) United States Patent
Zielinska et al.

(10) Patent No.: US 9,370,199 B2
(45) Date of Patent: Jun. 21, 2016

(54) **STRAIN OF *LACTOBACILLUS BUCHNERI* A, COMPOSITION, A MULTI-COMPONENT PREPARATION FOR STARCH-RICH PLANT PRESERVATION, THEIR USE AND A METHOD FOR PLANT PRESERVATION**

(71) Applicant: Instytut Biotechnologii Przemyslu Rolno-Spozywczego, Warsaw (PL)

(72) Inventors: Krystyna Zielinska, Warsaw (PL); Agata Fabiszewska, Warsaw (PL); Krystyna Stecka, Warsaw (PL); Michal Swiatek, Stoczek Lukowski (PL)

(73) Assignee: INSTYTUT BIOTECHNOLOGII PRZEMYSLU ROLNO-SPOZYWCZEGO, Warsaw (PL)

( * ) Notice: Subject to any disclaimer, the term of this patent is extended or adjusted under 35 U.S.C. 154(b) by 0 days.

(21) Appl. No.: 14/182,892

(22) Filed: Feb. 18, 2014

(65) Prior Publication Data

US 2014/0178528 A1 Jun. 26, 2014

Related U.S. Application Data

(63) Continuation-in-part of application No. PCT/PL2013/000037, filed on Mar. 21, 2013.

(30) Foreign Application Priority Data

Nov. 22, 2012 (PL) ..................... P.401735

(51) Int. Cl.
| | |
|---|---|
| C12P 1/04 | (2006.01) |
| C12P 7/52 | (2006.01) |
| C12R 1/225 | (2006.01) |
| A23K 3/00 | (2006.01) |
| A23K 1/00 | (2006.01) |
| A23K 3/03 | (2006.01) |
| C12N 1/20 | (2006.01) |

(52) U.S. Cl.
CPC ................. *A23K 1/007* (2013.01); *A23K 3/035* (2013.01); *C12N 1/20* (2013.01); *C12R 1/225* (2013.01)

(58) Field of Classification Search
None
See application file for complete search history.

(56) References Cited

U.S. PATENT DOCUMENTS

| | | | |
|---|---|---|---|
| 6,326,037 B1 * | 12/2001 | Mann et al. ..................... 426/52 |
| 2005/0281917 A1 * | 12/2005 | Charley et al. .................. 426/53 |
| 2013/0330439 A1 * | 12/2013 | Owens et al. ..................... 426/2 |
| 2014/0342038 A1 * | 11/2014 | Lewis et al. ..................... 426/53 |

FOREIGN PATENT DOCUMENTS

WO  WO 2011159178 A1 * 12/2011

OTHER PUBLICATIONS

Suterska et al., "Effect of the Selected Strains From Lactobacillus Genus on the Limitation of Mould and Ochratoxin a Contamination of Silages From Meadow Sward", Journal of Research and Applications in Agricultural Engineering 2009, vol. 54, pp. 125-129.*
International Search Report for International application No. PCT/PL2013/000037.
Aug. 27, 2010 Wang w. Zhou z.: feed research institue, chinese acdemy of agricultural science, key laboratory for feed biotechnology of the minister of agriculture, No. 12, XP002698079, retrieved from EBI, Database accession No. HM162412.

* cited by examiner

*Primary Examiner* — Renee Claytor
*Assistant Examiner* — Michelle F Paguio Frising
(74) *Attorney, Agent, or Firm* — Vedder Price P.C.; Thomas J. Kowalski; Deborah L. Lu

(57) ABSTRACT

The object of the invention is a new strain of *Lactobacillus buchneri* A deposited in the Collection of Industrial Microorganisms in the Institute of Agricultural and Food Biotechnology in Warsaw, under the number KKP 2047 p. The invention also concerns composition and a multi-component preparation for starch-rich plant preservation comprising this new strain, uses thereof and the method of silage production or starch-rich plant preservation.

14 Claims, 4 Drawing Sheets

SEQUENCE LISTING

```
<160> NUMBER OF SEQ ID NOS: 1

<210> SEQ ID NO 1
<211> LENGTH: 1445
<212> TYPE: DNA
<213> ORGANISM: Lactobacillus buchneri

<400> SEQUENCE: 1
atgcagtcga cgcgtctccg ttgatgattt taggtgcttg cacttgaaag atttaacatt     60
gagacgagtg gcgaactggt gagtaacacg tgggtaacct gcccttgaag taggggataa    120
cacttggaaa caggtgctaa taccgtataa caaccaaaac cacctggttt tggtttaaaa    180
gacggcttcg gctgtcactt taggatggac ccgcggcgta ttagcttgtt ggtaaggtaa    240
cggcctacca aggcgatgat acgtagccga cctgagaggg taatcggcca cattgggact    300
gagacacggc ccaaactcct acgggaggca gcagtaggga atcttccaca atggacgaaa    360
gtctgatgga gcaacgccgc gtgagtgatg aagggtttcg gctcgtaaaa ctctgttgtt    420
ggagaagaac aggtgtcaga gtaactgttg acatcttgac ggtatccaac cagaaagcca    480
cggctaacta cgtgccagca gccgcggtaa tacgtaggtg gcaagcgttg tccggattta    540
ttgggcgtaa agcgagcgca ggcggttttt taggtctgat gtgaaagcct ttcggcttaa    600
ccggagaagt gcatcggaaa ccgggagact tgagtgcaga agaggacagt ggaactccat    660
gtgtagcggt gaaatgcgta gatatatgga agaacaccag tggcgaaggc ggctgtctgg    720
tctgtaactg acgctgaggc tcgaaagcat gggtagcgaa caggattaga tacccctggta   780 gtccatgccg taaacgatga gtgctaagtg ttggagggtt tccgcccttc agtgctgcag    840
ctaacgcatt aagcactccg cctggggagt acgaccgca aggttgaaac tcaaaggaat     900 tgacggggc ccgcacaagc ggtggagcat gtggtttaat tcgatgctac gcgaagaacc    960
ttaccaggtc ttgacatctt ctgccaacct aagagattag gcgttccctt cggggacaga   1020
atgacaggtg gtgcatggtt gtcgtcagct cgtgtcgtga gatgttgggt taagtcccgc   1080
aacgagcgca acccttattg ttagttgcca gcattcagtt gggcactcta gcaagactgc   1140
cggtgacaaa ccggaggaag gtggggatga cgtcaaatca tcatgcccct tatgacctgg   1200
gctacacacg tgctacaatg gacggtacaa cgagtcgcga aaccgcgagg tcaagctaat   1260
ctcttaaagc cgttctcagt tcggattgta ggctgcaact cgcctacatg aagttggaat   1320
```

```
cgctagtaat cgtggatcag catgccacgg tgaatacgtt cccgggcctt gtacacaccg    1380
cccgtcacac catgagagtt tgtaacaccc aaagccggtg aggtaacctt cgggaccagc    1440
cgtct                                                                1445
```

STRAIN OF *LACTOBACILLUS BUCHNERI* A, COMPOSITION, A MULTI-COMPONENT PREPARATION FOR STARCH-RICH PLANT PRESERVATION, THEIR USE AND A METHOD FOR PLANT PRESERVATION

RELATED APPLICATIONS AND INCORPORATION BY REFERENCE

This application is a continuation-in-part application of international patent application Serial No. PCT Patent Application PCT/PL2013/000037 filed 21 Mar. 2013, which claims benefit of Polish patent application Serial No. P.401735 filed 22 Nov. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The object of the invention is a new strain of *Lactobacillus buchneri* A, deposited in the Collection of Industrial Microorganisms in the Institute of Agricultural and Food Biotechnology in Warsaw, under the number KKP 2047 p, a composition and a multi-component preparation for starch-rich plant preservation, their use and a method for plant preservation.

BACKGROUND OF THE INVENTION

Currently, there is a high demand for enrichment of starter cultures for preparations for forage ensiling with new, not genetically modified strains of lactic acid bacteria isolated from the natural environment. The involvement of these strains in forage ensiling processes contributes to the improvement in quality, aerobic stability and nutritive value of silage, as well as being safe for animals and natural environment.

Patent PL209677 relates to the strain *Lactobacillus buchneri* KPP 907 p, which is characterized by the ability to synthesize 1,2-propanediol, without showing, however, any ability to metabolize it and utilize it in bacterial growth.

In modern methods of roughage ensiling, additives of bacterial or bacterial-enzymatic preparations are used in order to improve silage quality. Preparations of this type are in numerous patents, e.g. EP0369198 and EP0563133, as well as PL180272, PL 180 329, PL 190232, PL 208392, PL 209677, PL 210287, PL 212635, WO 2008073848 A1, WO 9729644 A1.

U.S. Pat. No. 6,403,084 relates to inoculants for forage ensiling, which relates to mixed cultures of homofermentative and heterofermentative lactic acid bacteria of the *Lactobacillus* genus and the *Enterococcus faecium* species. Some of the strains are genetically modified by chemical or radiation mutagenesis, conjugation, transduction or transformation, and thus should not be used in countries where use of GMO in agriculture is prohibited, such as Poland. Such strains are also not allowed in organic farming.

Citation or identification of any document in this application is not an admission that such document is available as prior art to the present invention.

SUMMARY OF THE INVENTION

The aim of the invention was to isolate, from ensiled corn grains, a new strain of the *Lactobacillus buchneri* species that, without genetic modifications, will be characterized by a desired efficacy of 1,2-propanediol synthesis and the ability to metabolize it to propionic acid, both compounds improving the durability and aerobic stability of starch-rich fodder, as well as the design of a multi-component preparation for ensiling process stimulation and improvement of starch-rich silage durability. The new strain of *Lactobacillus buchneri* species, due to its properties, will preferably be used for preparation of silage, as well as starch-rich plant silage for biogas production.

The *Lactobacillus buchneri* A strain according to the invention was isolated from ensiled corn grains, which were stored for three years in anaerobic conditions, by multiple selection of colonies growing on solid MRS media, containing 1,2-propanediol as carbon source.

The first object of the invention is a new bacterial strain, which was defined as *Lactobacillus buchneri* A and deposited in the Collection of Industrial Microorganisms in the Institute of Agricultural and Food Biotechnology in Warsaw, under the number KKP 2047 p.

The second object of the invention is a composition which may comprise a bacterial strain of *Lactobacillus buchneri* A, deposited in the Collection of Industrial Microorganisms in the Institute of Agricultural and Food Biotechnology in Warsaw, under the number KKP 2047 p.

The invention also relates to a multi-component preparation for starch-rich plant preservation, which may comprise a bacterial starter culture of the *Lactobacillus* genus, the starter culture consisting of a mixture of strains: *Lactobacillus buchneri* A KKP 2047 p, *Lactobacillus plantarum* K KKP 593 p, *Lactobacillus plantarum* S KKP 2021 p, *Lactobacillus fermentum* N KKP 2020 p, *Lactobacillus reuteri* M KKP 2048 p, wherein the preparation preferably also contains enzymes, vitamins, carriers and emulsifiers.

In the multi-component preparation the weight ratio of individual strains of *Lactobacillus buchneri* A KKP 2047 p, *Lactobacillus plantarum* K KKP 593 p, *Lactobacillus plantarum* S KKP 2021 p, *Lactobacillus fermentum* N KKP 2020 p, *Lactobacillus reuteri* M KKP 2048 p in the mixture is from 1.8 to 2.5:from 0.8 to 1.2:from 0.6 to 1:from 0.8 to 1.2:from 1 to 1.2, most preferably 2:1:1:1:1, wherein the preparation contains from 0.5% to 1% w/w of enzymes with main activities: endo-1,4-β-D-glucanase EC 3.2.1.4, beta-glucanase EC 3.2.1.6, xylanase EC 3.2.1.8 and vitamin $B_{12}$ in quantity from 0.05% to 0.1% w/w, as well as carriers in quantity from 88% to 90% w/w.

Preferably, carriers in the preparation are soluble starch, sucrose, glucose and lactose, and preferably lecithin is used as an emulsifier.

The invention also relates to the use of the new bacterial strain of *Lactobacillus buchneri* A KKP 2047 p, the composition containing *Lactobacillus buchneri* A KKP 2047 p, or the multi-component preparation according to the invention for the stimulation of ensiling process, preservation and/or improvement of starch-rich plant durability.

Preferably, the starch-rich plant is corn.

The invention also relates to a method of silage production or starch-rich plant preservation, which may comprise a step of adding the new bacterial strain of *Lactobacillus buchneri* A KKP 2047 p, the composition containing *Lactobacillus buchneri* A KKP 2047 p, or the multi-component preparation according to the invention, to a starch-rich plant material. Preferably, the addition step is performed by spraying after dissolving the preparation in water. A particularly preferable starch-rich plant material are corn grains.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with the Collection of Industrial Microorganisms in the Institute of Agricultural and Food Biotechnology in Warsaw, under deposit accession number KKP 2047 p, K KKP 593 p, S KKP 2021 p, N KKP 2020 p and M KKP 2048 p were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

The invention will be easier to understand with regard to the description below, constituting however only an example of an embodiment, with reference to figures, where.

DETAILED DESCRIPTION OF THE INVENTION

The new strain of *Lactobacillus buchneri* A according to the invention, was isolated from ensiled corn grains, which were stored for three years in anaerobic conditions, by multiple selection of colonies growing on solid MRS media, containing 1,2-propanediol as carbon source. The new isolated strain was identified as *Lactobacillus buchneri* A and deposited in the Collection of Industrial Microorganisms in the Institute of Agricultural and Food Biotechnology, under the number KKP 2047 p.

The strain of *Lactobacillus buchneri* A KKP 2047 p is characterized by the following morphological features:

bacterial colonies growing in anaerobic conditions on agar-solidified MRS medium, specific for the *Lactobacillus* genus (De Man J. D., Rogosa M., Sharpe M. E.: A medium for the cultivation of Lactobacilli, J. Appl. Bact., 23, 130-135, 1960) have an oval shape, are white, with a size of about 0.5 mm.

bacterial cells do not produce spores, are gram-positive, have a form of short rods, occur singly or together in chains, which is characteristic for the *Lactobacillus buchneri* species. Optimal temperature of the strain's growth is 35° C. On the basis of the obtained results of lactic acid fermentation of 49 carbohydrates contained in the API test and computer data analysis, it was established that the new bacterial strain isolated from ensiled corn grains ferments the following carbohydrates: glucose, fructose, galactose, D-xylose, L-arabinose, ribose, maltose, melibiose, sucrose, melicitose and raffinose.

Genetic identification was performed by sequencing of a 16S rRNA gene fragment and comparison of obtained results with the ones published in genetic databases for genetic identification of this species.

The new bacterial strain was identified as *Lactobacillus buchneri* with 99% compatibility with the test strain species.

Figure 1:
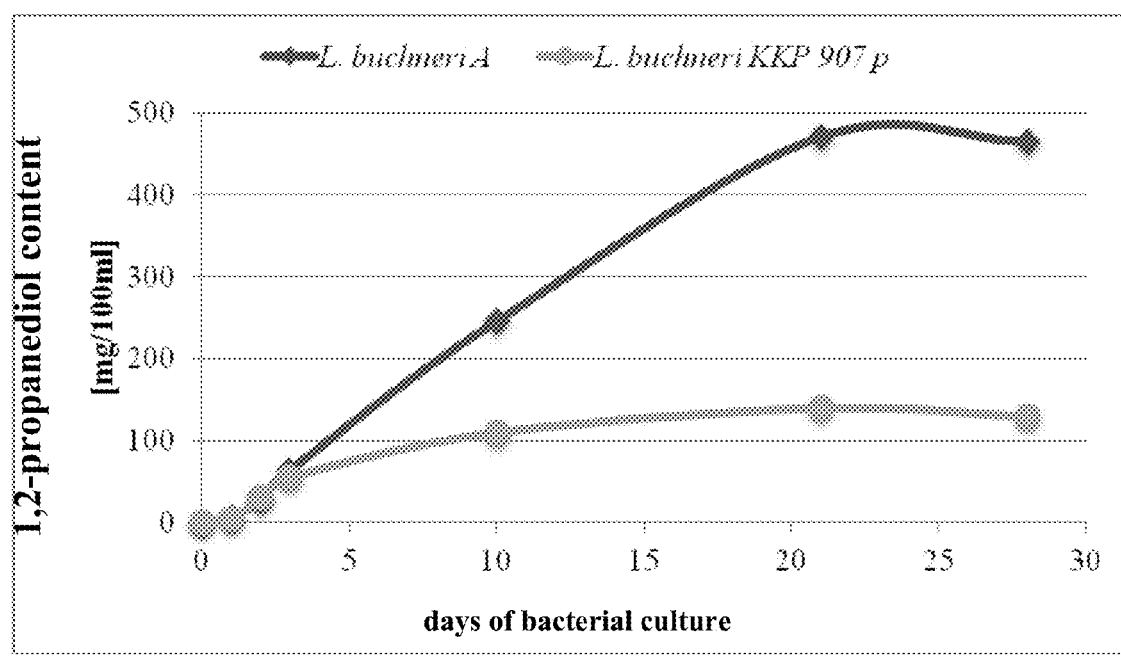
FIG. 1 shows a comparison of 1,2-propanediol synthesis dynamics in MRS medium during 28 days of culture of *L. buchneri* A KPP 2047 p and *L. buchneri* KKP 907 p strains.
Figure 2:
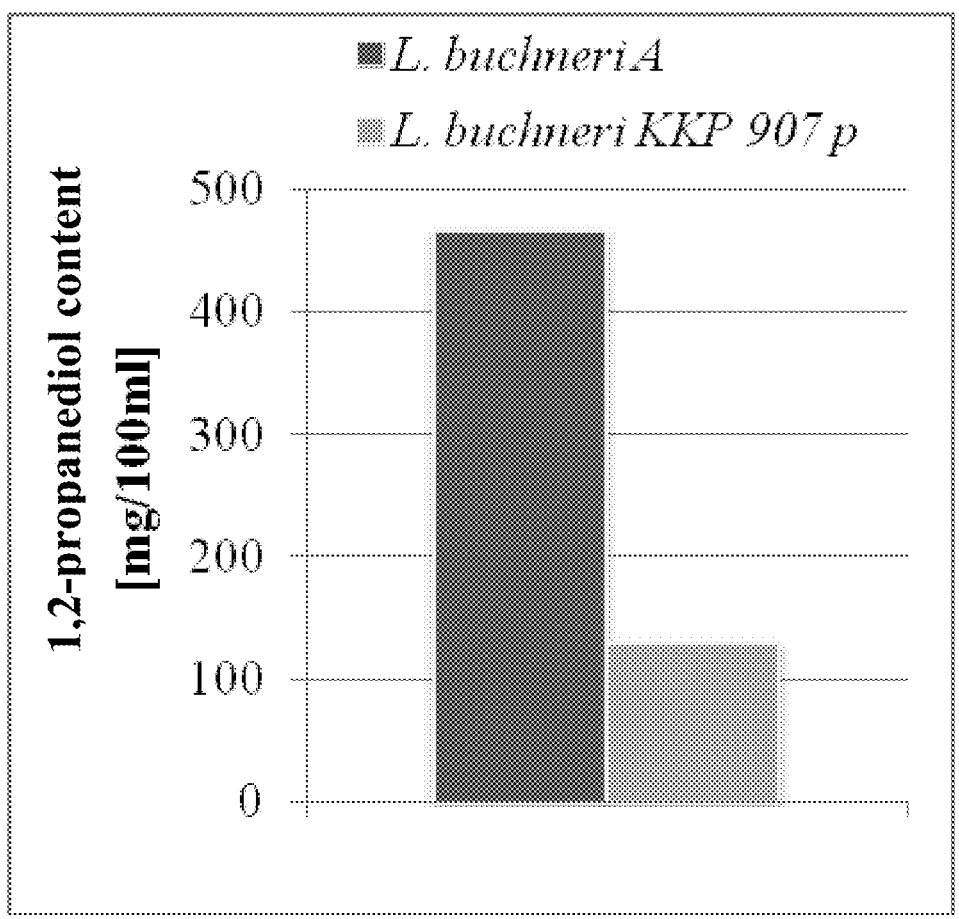
FIG. 2 shows a comparison of 1,2-propanediol content in MRS medium on the 28th day of culture of *L. buchneri* A KPP 2047 p and *L. buchneri* KKP 907 p strains.

The results of genetic analysis of a 16 S rRNA fragment from the strain *Lactobacillus buchneri* A KKP 2047 p defined in this invention, are shown in SEQ ID NO:1. The strain according to the invention, in comparison to the known strain *Lactobacillus buchneri* KPP 907 p, is characterized by more than three times higher efficiency of 1,2-propanediol synthesis, as shown on FIGS. 1 and 2.

Unexpectedly, the new strain *Lactobacillus buchneri* A KKP 2047 p also has the ability to use 1,2-propanediol for bacterial growth, and therefore to metabolize it, which is not an obvious feature for the *Lactobacillus buchneri* species.

Figure 3:
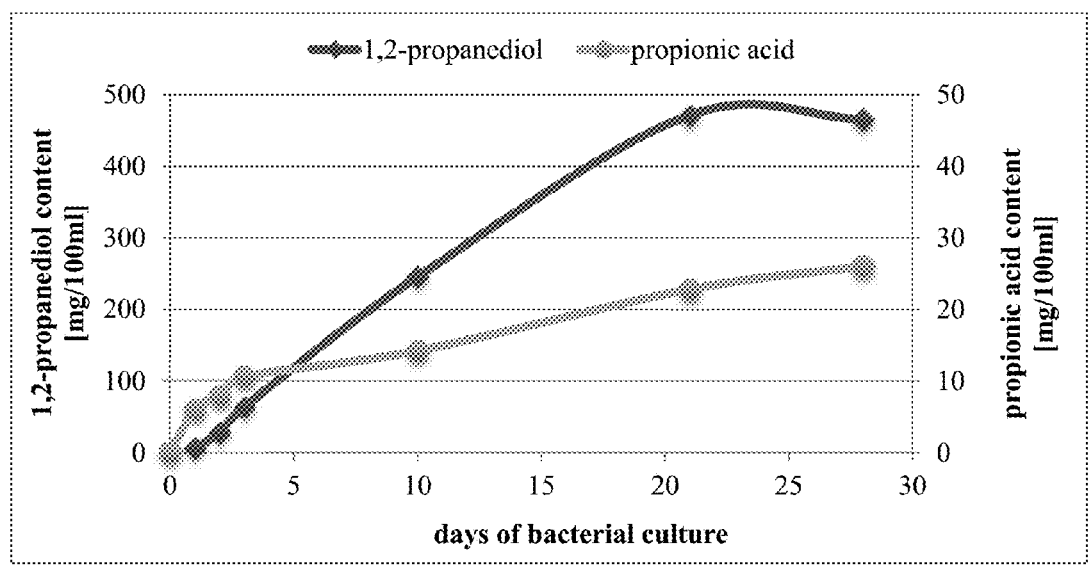
FIG. 3 shows a dynamics of changes in the 1,2-propandiol and propionic acid content in culture of the *L. buchneri* A KPP 2047 p strain during 28 days of culture in MRS medium.

During culture of the bacteria of the *Lactobacillus buchneri* A KKP 2047 p strain according to the invention, in MRS medium with glucose as a carbon source, the content of lactic acid and acetic acid was increasing until the $3^{rd}$ day, and then fell, while the content of 1,2-propanediol and propionic acid was increasing until the $21^{st}$ day of culture, whereupon the content of 1,2-propanediol showed a downward trend, while the content of propionic acid continued to increase, reaching the value of 26 mg/100 ml of medium on the $28^{th}$ day of culture (FIG. 3).

Figure 4:
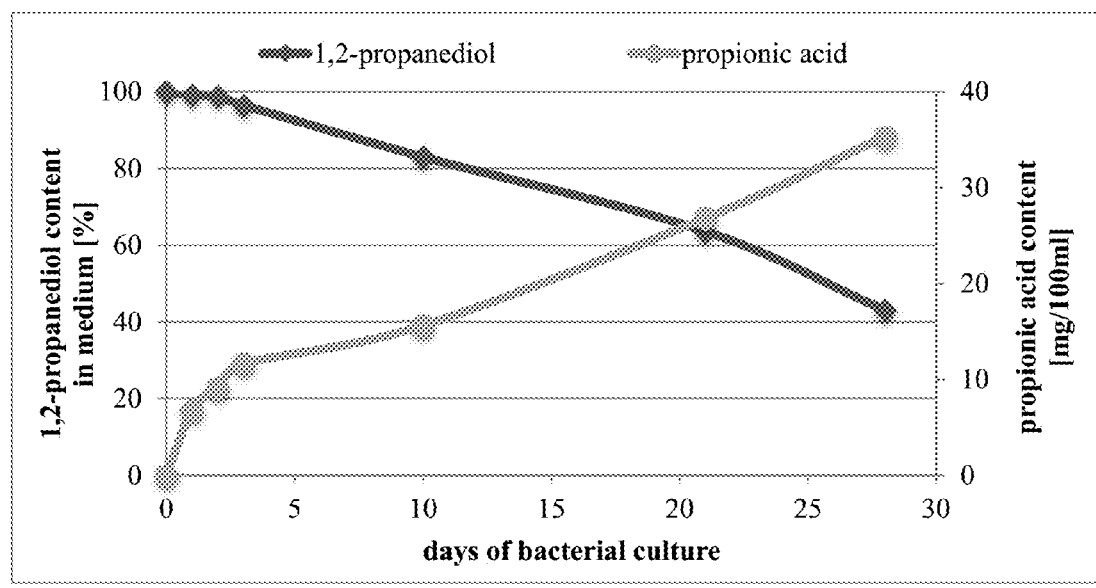
FIG. 4 shows a dynamics of 1,2-propanediol use and propionic acid synthesis by the *L. buchneri* A KPP 2047 p strain during 28 days of culture in medium with glucose and 1,2-propanediol (in molar ratio 1:2).

In bacterial culture for 28 days, temperature of 35° C., in medium containing glucose and 1,2-propanediol (in molar ratio 1:2), 57% of 1,2-propanediol content was used for the production of biomass and organic acids, including propionic acid, wherein the effectiveness of propionic acid synthesis was higher than during culture of *Lactobacillus buchneri* A KKP 2047 p in medium with glucose, without the addition of 1,2-propanediol (FIG. 4).

Another object of the invention is a multi-component preparation for starch-rich plant preservation, which may comprise a bacterial starter culture of the *Lactobacillus* genus, the starter culture consisting of a mixture of strains: *Lactobacillus buchneri* A KKP 2047 p, *Lactobacillus plantarum* K KKP 593 p, *Lactobacillus plantarum* S KKP 2021 p, *Lactobacillus fermentum* N KKP 2020 p, *Lactobacillus reuteri* M KKP 2048 p, wherein the preparation preferably also contains enzymes, vitamins, carriers and emulsifiers.

The preferable preparation according to the invention contains a bacterial starter culture of the *Lactobacillus* genus, enzymes, vitamins, as well as carriers and an emulsifier, and is characterized by the fact that the starter culture which may comprise the strains: *Lactobacillus buchneri* A KKP 2047 p, *Lactobacillus plantarum* K KKP 593 p, *Lactobacillus plantarum* S KKP 2021 p, *Lactobacillus fermentum* N KKP 2020 p, *Lactobacillus reuteri* M KKP 2048 p, wherein the weight ratio of individual strains in the mixture is from 1.8 to 2.5: from 0.8 to 1.2:from 0.6 to 1.0:from 0.8 to 1.2:from 1.0 to 1.2, most preferably 2:1:1:1:1.

In addition, the multi-component preparation prepared according to the invention contains from 0.5% to 1.0% w/w of enzymes with main activities: endo-1,4-β-D-glucanase EC 3.2.1.4 (cellulase), beta-glucanase EC 3.2.1.6 (endo-1,3(4)-β-glucanase), xylanase EC 3.2.1.8 (endo-1,4-β-xylanase) and vitamin $B_{12}$ in quantity from 0.05% to 0.1% w/w, as well as carriers and an emulsifier in quantity from 88% to 90% w/w.

Preferable carriers in the preparation are soluble starch, sucrose, glucose and lactose, and preferably lecithin is used as an emulsifier.

All strains used in the multi-component preparation were isolated from plant environment, have GRAS status and are deposited in the Collection of Industrial Microorganisms in the Institute of Agricultural and Food Biotechnology.

Unexpectedly, it has been found that a synergistic activity of bacterial strains contained in the multi-component preparation with enzymes, which is particularly advantageous in the presence of a coenzyme for the propionic acid synthesis reaction—vitamin $B_{12}$, results in multidirectional activity of the preparation, that inhibits mold and pathogenic bacteria growth, reduces the level of contamination by aflatoxin B1 and ochratoxin A and increases the durability of starch-rich feed silage, e.g. corn grains and whole corn plants, without loss of quality or energy value of silage, for at least three years, and extends their aerobic stability after opening the silos to 16 days.

The invention is illustrated by non-limiting examples of embodiments.

EXAMPLES

Example 1

Characterization of the *Lactobacillus buchneri* A KKP 2047 p Strain

Table 1 shows the results of lactic acid [L+D], acetic acid, 1,2-propanediol and propionic acid synthesis by the new strain *Lactobacillus buchneri* A KKP 2047 p (MRS medium (by Man, Rogosa and Sharpe, 1960), carbon source: glucose), culture temperature 35° C., duration of culture 28 days, individual samples for study were collected on 1, 2, 3, 10, 21 and 28 day of culture.

TABLE 1

The dynamics of synthesis of organic acids, 1,2-propanediol and growth for *Lactobacillus buchneri* A KKP 2047 p in MRS medium (by Man, Rogosa and Sharpe, 1960).
Duration of culture 28 days, temperature 35° C., the results shown are average of three experiments.

| MRS | Days of bacterial culture | | | | | |
|---|---|---|---|---|---|---|
| | 1 | 2 | 3 | 10 | 21 | 28 |
| | Lactic acid content [L + D] | | | | | |
| g/100 ml | 1.55 | 1.60 | 1.73 | 1.60 | 1.48 | 1.29 |
| | Acetic acid content | | | | | |
| g/100 ml | 0.34 | 0.38 | 0.40 | 0.38 | 0.36 | 0.35 |
| | 1,2-propanediol content | | | | | |
| mg/100 ml | 5.72 | 27.93 | 63.51 | 245.28 | 471.10 | 465.00 |
| | Propionic acid content | | | | | |
| mg/100 ml | 6.0 | 7.9 | 10.6 | 14.2 | 22.8 | 26.0 |
| | Bacterial biomass | | | | | |
| Number of bacterial cfu/ml | $2.8 \times 10^9$ | $4.8 \times 10^9$ | $6.2 \times 10^9$ | $1.2 \times 10^9$ | $3.6 \times 10^8$ | $1.6 \times 10^8$ |

During culture of the bacteria of the *Lactobacillus buchneri* A KKP 2047 p strain, in MRS medium with glucose as a carbon source, the content of lactic acid and acetic acid was increasing until the $3^{rd}$ day, and then fell, while the content of 1,2-propanediol and propionic acid was increasing until the $21^{st}$ day of culture, whereupon the content of 1,2-propanediol showed a downward trend, while the content of propionic acid continued to increase, reaching the value of 26 mg/100 ml of medium on the $28^{th}$ day of culture (Table 1 and FIG. 3).

Table 2 shows the results of lactic acid [L+D], acetic acid and propionic acid content, as well as the percentage utilization of 1,2-propanediol added to the medium, by the bacteria of *Lactobacillus buchneri* A KKP 2047 p strain, cultured in MRS medium, where portion of glucose was replaced with 1,2-propanediol (the molar ratio of glucose to 1,2-propanediol was 1:2). The bacteria were cultured in temperature of 35° C., up to 28 days.

TABLE 2

The influence of 1,2-propanediol on bacterial biomass growth and metabolite synthesis by *Lactobacillus buchneri* A KKP 2047 p. Duration of culture 28 days, temperature of 35° C., the results shown are average of three experiments.

| MRS with 1,2-propanediol | Days of bacterial culture | | | | | |
|---|---|---|---|---|---|---|
| | 1 | 2 | 3 | 10 | 21 | 28 |
| Lactic acid content [L + D] | | | | | | |
| g/100 ml | 1.10 | 1.24 | 1.30 | 1.26 | 1.16 | 1.11 |
| Acetic acid content | | | | | | |
| g/100 ml | 0.49 | 0.54 | 0.56 | 0.52 | 0.40 | 0.36 |
| Propionic acid content | | | | | | |
| mg/100 ml | 6.8 | 9.1 | 11.6 | 15.6 | 26.8 | 36.5 |
| Bacterial biomass | | | | | | |
| number of bacterial cfu/ml | $1.2 \times 10^9$ | $2.0 \times 10^9$ | $2.2 \times 10^9$ | $1.4 \times 10^9$ | $5.6 \times 10^8$ | $1.2 \times 10^8$ |
| Degree of 1,2-propanediol utilization | | | | | | |
| percentage | 0.9 | 1.2 | 3.5 | 17.0 | 36.4 | 57.0 |

In bacterial culture conditions for 28 days, in medium containing glucose and 1,2-propanediol (in molar ratio 1:2), 57% of 1,2-propanediol content was used for the production of biomass and organic acids, including propionic acid, wherein the effectiveness of propionic acid synthesis was higher than during culture of *Lactobacillus buchneri* A KKP 2047 p in medium with glucose, without the addition of 1,2-propanediol (Table 2 and FIG. 4).

Example 2

Conditions of Biomass Propagation of *Lactobacillus buchneri* A KKP 2047 p Strain and Preparation of Dry Formulation After multiplication of the inoculum (test tube stage and flask stage in three steps) bacterial culture was carried out in a medium of the following composition (in g/l of water): sucrose—20, yeast extract—10, corn steep liquor—5, diammonium phosphate—0.2, magnesium sulphate—0.08, ammonium sulphate—0.35, manganese sulphate—0.01; in fermenters with a capacity of 150 l at 35° C., pH controlled with aqueous ammonia to the value 5.8.

Centrifuge with a spin ratio above 13000×g was used for biomass separation.

After culture in conditions given above, 1000 g of bacterial biomass was obtained with a 30% DM (dry mass) content.

Bacterial biomass obtained after centrifugation, after mixing with carriers such as potato soluble starch, lactose, glucose and sucrose, was treated with fluidization drying in temperature not exceeding 40° C. Dry granular bacterial preparation with dry mass content of around 94% contained $2 \times 10^9$ bacterial colony forming units in 1 g.

Example 3

Production of Multi-Component Bacterial Preparation

The multi-component bacterial preparation according to the invention was obtained in such a way that for every individual strain the bacterial preparation was produced separately in granular form, by methods described in Example 2.

The obtained preparation for each bacterial strain was characterized by the dry mass content of 93-94%.

Afterwards, the dried preparations of the strains: *Lactobacillus buchneri* A 2047 p, *Lactobacillus plantarum* K KKP 593 p, *Lactobacillus plantarum* S KKP 2021, *Lactobacillus fermentum* N KKP 2020 p, *Lactobacillus reuteri* M KKP 2048 p were mixed in weight ratio 2:1:1:1:1 and supplemented with 1% w/w of enzymatic preparation with main activities: endo-1,4-β-D-glucanase EC 3.2.1.4, beta-glucanase EC 3.2.1.6, xylanase EC 3.2.1.8 and vitamin $B_{12}$ in quantity 0.1% w/w. The number of bacterial colony forming units (cfu) was around $2 \times 10^9$ in 1 g of dry preparation.

Example 4

The multi-component bacterial preparation obtained in example 3 was used for corn grain silage production. The preparation was used in spray form, after dissolving in drinking water, in a dose of 5 g per 1 ton of corn grain silage.

Silage produced with and without the addition of the preparation was stored in silos for 3 years, then after silo opening its content of: lactic, acetic and butyric acids and 1,2-propanediol, as well as its metabolites: 1-propanol and propionic acid was determined. The silage quality was evaluated according to Flieg-Zimmer scale (Zimmer E., Wirtschaftseig. Futter, 12, p. 299, 1966) and digestibility of dry organic matter, content of starch and protein, and aerobic stability of silage were compared. The obtained results are shown in Tables 3 and 4.

TABLE 3

Organic acids, 1,2-propanediol and 1-propanol content in corn grain silage, with or without the addition of the preparation, after 3-year storage period. The results shown are average of three experiments in production scale.

| Corn grain silage | Organic acid content [%] | | | Metabolite content [mg/100 g] | | |
|---|---|---|---|---|---|---|
| | pH | lactic | acetic | butyric | 1,2-propanediol | 1-propanol | propionic acid |
| without the preparation | 5.66 | 0.32 | 0.49 | 1.25 | 1.2 | none | none |
| with the preparation | 4.06 | 1.73 | 0.39 | none | 25.47 | 70.33 | 54.80 |

Under the influence of the multi-component preparation the corn grain silage was characterized by very high quality, high content of: lactic acid [1.73%] and propionic acid [54.8 mg/100 g]. However, the silage without the addition of the preparation was characterized by poor quality and after three years of storage was not suitable for animal feed.

TABLE 4

Influence of the multi-component preparation on starch and total protein content, digestibility of dry organic mass and aerobic stability of corn grain silage. The results shown are average of three experiments in production scale.

| Silage: | Humidity [%] | Starch content [%] | Dry organic mass digestibility [%] | Total protein content [%] | Aerobic stability in days |
|---|---|---|---|---|---|
| without the preparation | 40.0 | 50.4 | 81.4 | 5.27 | 4 |
| with the preparation | 36.8 | 54.5 | 85.4 | 6.66 | 16 |

Under the influence of the multi-component preparation digestibility of dry organic mass (DM) of silage increased by 4%, while starch and protein loss was limited by 7.5 and 21.0% respectively, in relation to silage without the preparation. High lactic acid and acetic acid content in silage with the preparation has ensured high quality of corn grain silage, even after 3 years of storage. The addition of the preparation has improved silage aerobic stability. Silage with the addition of the preparation in quantity of 5.0 g/t showed aerobic stability for 16 days after opening the silo, which is a sufficient period for its use as animal feed.

In parallel microbiological purity of silage produced with or without the preparation was assessed and contamination with the *Salmonella* sp., *Escherichia coli* bacteria and molds was determined. The results on the influence of the preparation on the improvement in the purity of silage is shown in Table 5.

TABLE 5

Influence of the preparation on the improvement in corn grain silage purity. The results shown are average of three experiments in production scale.

| Corn grain silage: | Number of pathogenic bacteria and molds in silage, log cfu/g DM of silage | | | Mycotoxin content in DM of silage, ppb (µg/kg) | |
|---|---|---|---|---|---|
| | *Salmonella* sp | *Escherichia coli* | molds | aflatoxin $B_1$ | ochratoxin A |
| without the preparation | 2.30 | 3.00 | 5.60 | 9.7 | 13.2 |
| with the preparation | none | none | 2.30 | 2.5 | 3.3 |

In corn grain silage with the addition of the multi-component preparation, pathogenic bacteria of the *Salmonella* sp. genus and the *Escherichia coli* species were eliminated in 100%. The preparation also caused a reduction in the number of molds by around 3 log cfu/g DM of silage and a reduction in aflatoxin $B_1$ and ochratoxin A by around 75% in comparison to silage without the preparation.

Animal feed contaminated with molds, aflatoxin $B_1$, ochratoxin A and pathogenic microorganisms, after the lactic acid fermentation process involving the multi-component preparation may safely be used in feeding of livestock.

The invention is further described by the following numbered paragraphs:

1. A new bacterial strain of *Lactobacillus buchneri* A deposited in the Collection of Industrial Microorganisms in the Institute of Agricultural and Food Biotechnology in Warsaw, under the number KKP 2047 p.

2. A composition comprising a bacterial strain of *Lactobacillus buchneri* A, deposited in the Collection of Industrial Microorganisms in the Institute of Agricultural and Food Biotechnology in Warsaw, under the number KKP 2047 p.

3. A multi-component preparation for starch-rich plant preservation, comprising a bacterial starter culture of the *Lactobacillus* genus, characterized in that the starter culture consists of a mixture of strains: *Lactobacillus buchneri* A KKP 2047 p, *Lactobacillus plantarum* K KKP 593 p, *Lactobacillus plantarum* S KKP 2021 p, *Lactobacillus fermentum* N KKP 2020 p, *Lactobacillus reuteri* M KKP 2048 p, wherein the preparation preferably also contains enzymes, vitamins, carriers and emulsifiers.

4. The multi-component preparation according to paragraph 3, characterized in that the weight ratio of individual strains of *Lactobacillus buchneri* A KKP 2047 p, *Lactoba-* cillus plantarum K KKP 593 p, *Lactobacillus plantarum* S KKP 2021 p, *Lactobacillus fermentum* N KKP 2020 p, *Lactobacillus reuteri* M KKP 2048 p in the mixture is from 1.8 to 2.5:from 0.8 to 1.2:from 0.6 to 1:from 0.8 to 1.2:from 1 to 1.2, most preferably 2:1:1:1:1, wherein the preparation contains from 0.5% to 1% w/w of enzymes with main activities: endo-1,4-β-D-glucanase EC 3.2.1.4, beta-glucanase EC 3.2.1.6, xylanase EC 3.2.1.8 and vitamin $B_{12}$ in quantity from 0.05% to 0.1% w/w, as well as carriers in quantity from 88% to 90% w/w.

5. The preparation according to paragraphs 3-4, characterized in that the carrier composition includes: soluble starch, sucrose, glucose and lactose.

6. The preparation according to paragraphs 3-5, characterized in that the emulsifier is lecithin.

7. Use of the new bacterial strain as defined in paragraph 1, the composition as defined in paragraph 2, multi-component preparation as defined in any one of paragraphs 3 to 4 for the stimulation of ensiling process, preservation and/or improvement of starch-rich plant durability.

8. The use of paragraph 7, characterized in that the starch-rich plant is corn, preferably corn grains.

9. A method of silage production or starch-rich plant preservation, characterized in that it comprises a step of adding the new bacterial strain as defined in paragraph 1, the composition as defined in paragraph 2, the multi-component preparation as defined in any one of paragraphs 3 to 4 to a starch-rich plant material.

10. The method of paragraph 9, characterized in that the addition step is performed by spraying after dissolving the preparation in water.

11. The method of paragraphs 9-10, characterized in that the starch-rich plant material is corn, preferably corn grains.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for stimulation of ensiling process, preservation and/or improvement of starch-rich plant durability comprising adding a bacterial strain of *Lactobacillus buchneri* A deposited in the Collection of Industrial Microorganisms in the Institute of Agricultural and Food Biotechnology in Warsaw, under the number KKP 2047 p to a starch-rich plant material.

2. The method of claim 1, wherein the starch-rich plant is corn.

3. The method of claim 2, wherein the corn is a corn grain.

4. A method for stimulation of ensiling process, preservation and/or improvement of starch-rich plant durability comprising adding a multi-component preparation comprising a bacterial starter culture of the *Lactobacillus* genus, wherein the starter culture comprises *Lactobacillus buchneri* A KKP 2047 p, *Lactobacillus plantarum* K KKP 593 p, *Lactobacillus plantarum* S KKP 2021 p, and *Lactobacillus fermentum* N KKP 2020 p, and *Lactobacillus reuteri* M KKP 2048 p, wherein the preparation optionally further comprises enzymes, vitamins, carriers and emulsifiers, to a starch-rich plant material.

5. The method of claim 4, characterized in that the starch-rich plant is corn.

6. The method of claim 4, wherein the corn is a corn grain.

7. A method of silage production or starch-rich plant preservation, comprising adding a bacterial strain of *Lactobacillus buchneri* A deposited in the Collection of Industrial Microorganisms in the Institute of Agricultural and Food Biotechnology in Warsaw, under the number KKP 2047 p to a starch-rich plant material.

8. The method of claim 7, wherein the adding comprises spraying after dissolving the bacterial strain in water.

9. The method of claim 7, wherein the starch-rich plant material is corn.

10. The method of claim 9, wherein the corn is a corn grain.

11. A method of silage production or starch-rich plant preservation, comprising adding a multi-component preparation comprising a bacterial starter culture of the *Lactobacillus* genus, wherein the starter culture comprises *Lactobacillus buchneri* A KKP 2047 p, *Lactobacillus plantarum* K KKP 593 p, *Lactobacillus plantarum* S KKP 2021 p, *Lactobacillus fermentum* N KKP 2020 p, and *Lactobacillus reuteri* M KKP 2048 p, wherein the preparation optionally further comprises enzymes, vitamins, carriers and emulsifiers, to a starch-rich plant material.

12. The method of claim 11, wherein the adding comprises spraying after dissolving the preparation in water.

13. The method of claim 11, wherein the starch-rich plant material is corn.

14. The method of claim 13, wherein the corn is a corn grain.

\* \* \* \* \*